US000001531H

United States Statutory Invention Registration [19]

[11] Reg. Number: H1531

Blumentals et al.

[45] Published: May 7, 1996

[54] THERMOPHILIC DNA POLYMERASE

[76] Inventors: Ilse I. Blumentals, 20 Hunters Gate Ct., Silver Spring, Md. 20904; Roger S. Lasken, 16413 Keats Ter., Derwood, Md. 20855; Brian J. Schmidt, 13503 Crispin Way, Rockville, Md. 20853; Mary C. Longo, 5 Leatherbark Ct., Germantown, Md. 20874; A. John Hughes, Jr., 19444 St. Johnsbury La., Germantown, Md. 20876; Deb K. Chatterjee, 6 Forest Ridge Ct., N. Potomac, Md. 20878

[21] Appl. No.: 229,284

[22] Filed: Apr. 18, 1994

[51] Int. Cl.[6] ..... C12N 9/12

[52] U.S. Cl. ..... 435/194

[58] Field of Search ..... 435/194; 935/10, 935/14

[56] References Cited

U.S. PATENT DOCUMENTS

| | | | |
|---|---|---|---|
| 4,795,699 | 1/1989 | Tabor et al. | 435/5 |
| 4,889,818 | 12/1989 | Gelfand et al. | 435/194 |
| 5,047,342 | 9/1991 | Chatterjee | 435/194 |

FOREIGN PATENT DOCUMENTS

| | | |
|---|---|---|
| 0455430 | 11/1991 | European Pat. Off. . |
| 0547920 | 6/1993 | European Pat. Off. . |

OTHER PUBLICATIONS

Bergquist et al., "Genetics and Potential Biotechnological Applications of Thermophilic and Extremely Thermophilic Micro–organisms," *Biotech. & Genet. Eng. Rev.* 5:199–244 (Sep. 1987).

Blanco et al., "Evidence favouring the hypothesis of a conserved 3'–5' exonuclease active site in DNA–dependent DNA polymerases," *Gene* 112:139–144 (1992).

Bragger et al., "Very stable enzymes from extremely thermophilic archaebacteria and eubacteria," *Appl. Microbiol. Biotechnol.* 31:556–561 (1989).

Braithwaite & Ito, "Compilation, alignment, and phylogenetic relationships of DNA polymerases," *Nucl. Acids Res.* 21:787–802 (1993).

Chien et al., "Deoxyribonucleic Acid Polymerase from the Extreme Thermophile *Thermus aquaticus,*" *J. Bacteriol.* 127:1550–1557 (Sep. 1976).

Cowan et al., "An extremely thermostable extracellular proteinase from a strain of the archaebacterium Desulfurococcus growing at 88° C.," *J. Biochem.* 274:121–133 (1987).

Elie et al., "Thermostable DNA polymerase from the archaebacterium *Sulfolobus acidocaldarius:* Purification, characterization and immunological properties," *Eur. J. Biochem.* 178:619–626 (1989).

Gelfand & White, "Thermostable DNA Polymerases," in: *PCR Protocols: A Guide to Methods and Applications,* Innis et al. (eds.) Academic Press, Inc., San Diego, CA, pp. 129–130 (1990).

Kaboev et al., "Purification and Properties of Deoxyribonucleic Acid Polymerase from *Bacillus stearothermophilus,*" *J. Bacteriol.* 145:21–26 (Jan. 1981).

Kaledin et al., "Isolation and Properties of DNA Polymerase from Extremely Thermophilic Bacterium *Thermus aquaticus* YT1," *Biokhimiya* 45:644–651 (Apr. 1980).

Kelly & Deming, "Extremely Thermophilic Archaebacteria: Biological and Engineering Considerations," *Biotech. Prog.* 4:47–62 (Jun. 1988).

Klimczak et al., "Purification and Characterization of DNA Polymerase from the Archaebacteria *Methanobacterium thermoautotrophicum,*" *Biochem.* 25:4850–4855 (1986).

Lin et al., "Cloning and expression of T4 DNA polymerase," *Proc. Natl. Acad. Sci. USA* 84:7000–7004 (Oct. 1987).

Mattila et al., "Fidelity of DNA synthesis by the *Thermococcus litoralis* DNA polymerase—an extremely heat stable enzyme with proofreading activity," *Nucl. Acids Res.* 19:4967–4973 (Sep. 25, 1991).

Minkley et al., "*Escherichia coli* DNA Polymerase I," *J. Biol. Chem.* 259:10386–10392 (Aug. 25, 1984).

Patel et al., "Isolation of anaerobic, extremely thermophilic, sulphur metabolising archaebacteria from New Zealand hot springs," *New Zealand J. Marine & Freshwater Res.* 20:439–445 (1986).

Reddy et al., "Hyperexpression and purification of *Escherichia coli* adenylate cyclase using a vector designed for expression of lethal gene products," *Nucl. Acids Res.* 17:10473–10488 (1989).

Rossi et al., "Structure and Properties of a Thermophilic and Thermostable DNA Polymerase Isolated from *Sulfolobus solfataricus,*" *System. Appl. Microbiol.* 7:337–341 (1986).

Simpson et al., "Purification and some properties of a thermostable DNA polymerase from a Thermotoga species," *Biochem. Cell Biol.* 68:1292–1296 (1990).

Stenesh & Roe, "DNA Polymerases from Mesophilic and Thermophilic Bacteria: Purification and Properties of DNA Polymerase from *Bacillus licheniformis* and *Bacillus stearothermophilus,*" *Biochim. Biophys. Acta* 272:156–166 (19872).

*Primary Examiner*—Charles T. Jordan
*Assistant Examiner*—John R. Hardee

[57] ABSTRACT

The invention relates to a substantially pure thermostable DNA polymerase. Preferably, the DNA polymerase has a molecular weight of about 95 kilodaltons and is more thermostable than Taq DNA polymerase. The present invention also relates to cloning and expression of the DNA polymerase in *E. coli,* to DNA molecules containing the cloned gene, and to host cells which express said genes.

2 Claims, No Drawings

THERMOPHILIC DNA POLYMERASE

FIELD OF THE INVENTION

The present invention relates to a substantially pure thermostable DNA polymerase. Specifically, the DNA polymerase of the present invention is a Desulfurococcus strain Tok12-S1 DNA polymerase having a molecular weight of about 95 kilodaltons. The present invention also relates to cloning and expression of the this DNA polymerase in *E. coli,* to DNA molecules containing the cloned gene, and to hosts which express the gene.

BACKGROUND OF THE INVENTION

DNA polymerases synthesize the formation of DNA molecules which are complementary to a DNA template. Upon binding to a primer terminus of a DNA template, polymerases synthesize DNA in the 5' to 3' direction, successively adding nucleotides to the 3'-hydroxyl group of the growing strand. Thus, in the presence of deoxyribonucleoside triphosphates (dNTPs) and a primed template, a new DNA molecule, complementary to the single stranded DNA template, can by synthesized.

A number of DNA polymerases have been isolated from mesophilic microorganisms such as *E. coli.* A number of these mesophilic DNA polymerases have also been cloned. Lin et al. cloned and expressed T4 DNA polymerase in *E. coli* (*Proc. Natl. Acad. Sci. USA* 84:7000–7004 (1987)). Tabor et al. (U.S. Pat. No. 4,795,699) describes a cloned T7 DNA polymerase, while Minkley et al. (*J. Biol. Chem.* 259 (16):10386–10392 (1984)) and Chatterjee (U.S. Pat. No. 5,047,342) described cloning of *E. coli* DNA polymerase I and T5 DNA polymerase, respectively.

Although DNA polymerases from thermophiles are known, relatively little investigation has been done to isolate and clone these enzymes. Chien et al., *J. Bacteriol.* 127:1550–1557 (1976) describe a purification scheme for obtaining a polymerase from *Therrnus aquaticus.* The resulting protein had a molecular weight of about 63,000 daltons by gel filtration analysis and 68,000 daltons by sucrose gradient centrifugation. Kaledin et al., *Biokhymiya* 45:644–651 (1980) disclosed a purification procedure for isolating DNA polymerase from *T. aquaticus* YT1 strain. The purified enzyme was reported to be a 62,000 dalton monomeric protein. Gelland et al. (U.S. Pat. No. 4,889,818) cloned a gene encoding a thermostable DNA polymerase from *Thermus aquaticus.* The molecular weight of this protein was found to be about 86,000 to 90,000 daltons.

Thermophilic bacteria, other than *Thermus aquaticus,* have been isolated and a number of thermostable enzymes have been isolated from these organisms. Bragger et al., *Appl. Microbiol. Biotechnol.* 31:556–561 (1989) screened thirty-six thermophilic archaebacteria and nine extremely thermophilic eubacteria for extracellular amylase, protease, hemicellulase (xylanase), cellulase, pectinase and lipase activities.

DNA polymerases have been isolated from thermophilic bacteria including Thermotoga (Simpson et al., *Biochem. Cell. Biol.* 86:1292–1296 (1990)); *Bacillus stearothermophilus* (Stenesh et al., *Biochim. Biochys. Acta* 272:156–166 (1972); and Kaboev et al., *J. Bacteriol.* 145:21–26 (1981)); and several archaebacterial species (Rossi et al., *System. Appl. Microbiol.* 7:337–341 (1986); Klimczak et al., *Biochemistry* 25:4850–4855 (1986); and Elie et al., *Eur. J. Biochem.* 178:619–626 (1989)). Innis et al., In *PCR Protocol: A Guide To Methods and Amplification,* Academic Press, Inc., San Diego (1990) noted that there are several extreme thermophilic eubacteria and archaebacteria that are capable of growth at very high temperatures (Bergquist et al., *Biotech. Genet. Eng. Rev.* 5:199–244 (1987); and Kelly et al., *Biotechnol. Prog.* 4:47–62 (1988)) and suggested that these organisms may contain very thermostable DNA polymerases.

SUMMARY OF THE INVENTION

The present invention is directed to a DNA polymerase comprising amino acids 99 to 135 set forth in SEQ ID NO:2 or comprising amino acids 98 to 136 set forth in SEQ ID NO:2. More specifically, the DNA polymerase of the invention is isolated from Desulfurococcus strain Tok12-S1.

The DNA polymerase of the present invention is extremely thermostable, showing no loss of activity after 90 minutes at 95° C.

The DNA polymerase possesses a 3'–5' exonuclease activity. Thus, the DNA polymerase of the present invention has the ability to remove incorrectly incorporated nucleotides, an ability that the *Thermus aquaticus* DNA polymerase does not have.

The present invention is also directed to cloning a gene encoding the above-described DNA polymerase.

The invention also provides a nucleic acid probe molecule for specifically detecting the presence of the above-described DNA polymerase nucleic acid in a sample comprising a nucleic acid molecule sufficient to specifically detect by hybridization the presence of the above-described DNA polymerase nucleic acid in the sample.

The invention further provides a recombinant nucleic acid molecule comprising, 5' to 3', a promoter effective to initiate transcription in a host cell and the above-described isolated nucleic acid molecule.

The invention also provides a cell that contains the above-described recombinant nucleic acid molecule.

The invention further provides a non-human organism comprising a cell that contains the above-described recombinant nucleic acid molecule.

The invention also provides a method of producing the above-described DNA polymerase, the method comprising:

(a) culturing a cellular host comprising a gene encoding the DNA polymerase, wherein the gene is expressed; and (b) isolating the DNA polymerase from the host.

The invention further provides a method of synthesizing a double-stranded DNA molecule comprising:

(a) hybridizing a primer to a first DNA molecule; and (b) incubating the first DNA molecule in the presence of one or more deoxyribonucleoside triphosphates and the above-described DNA polymerase, under conditions sufficient to synthesize a second DNA molecule complementary to all or a portion of the first DNA molecule.

The invention also provides a method for purifying thermostable proteins larger than 50 kd in size in a sample, wherein the proteins are expressed in a therophilic host, comprising:

heating the sample and purifying the thermostable proteins by gel filtration.

DEFINITIONS

In the description that follows, a number of terms used in recombinant DNA technology are extensively utilized. In order to provide a clearer and consistent understanding of the specification and claims, including the scope to be given such terms, the following definitions are provided.

Isolated Nucleic Acid Molecule. An "isolated nucleic acid molecule," as is generally understood and used herein, refers to a polymer of nucleotides, and includes but is not limited to DNA and RNA.

DNA Segment. A DNA segment, as is generally understood and used herein, refers to a molecule comprising a linear stretch of nucleotides wherein the nucleotides are present in a sequence that may encode, through the genetic code, a molecule comprising a linear sequence of amino acid residues that is referred to as a protein, a protein fragment or a polypeptide.

Promoter. A DNA sequence generally described as the 5' region of a gene, located proximal to the start codon. At the promoter region, transcription of an adjacent gene(s) is initiated.

Gene. A DNA sequence that contains information necessary for expression of a polypeptide or protein. It includes the promoter and the structural gene as well as other sequences involved in expression of the protein.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC.

*Restriction Fragment.* The DNA molecules produced by digestion with a restriction endonuclease are referred to as restriction fragments. Any given genome may be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Oligonucleotide. "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide. As used herein "nucleotide" refers to a base-sugar-phosphate combination. Nucleotides are monomeric units of a nucleic acid sequence (DNA and RNA). The term nucleotide includes deoxyribonucleoside triphosphates such as dATP, dCTP, dUTP, dGTP, dTTP, or derivatives thereof. Such derivatives include, for example, dITP, αSdATP and 7-deaza-dGTP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Amplification. As used herein "amplification" refers to any in vitro method for increasing the number of copies of a nucleotide sequence with the use of a DNA polymerase. Nucleic acid amplification results in the incorporation of nucleotides into a DNA molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 30 to 100 "cycles" of denaturation and synthesis of a DNA molecule.

Primer. As used herein "primer" refers to a single-stranded oligonucleotide that is extended by covalent bonding of nucleotide monomers during amplification or polymerization of a DNA molecule.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Template. The term "template" as used herein refers to a double-stranded or single-stranded DNA molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to the template or a portion thereof. The newly synthesized DNA molecule, according to the invention, may be equal or shorter in length than the original DNA template. Mismatch incorporation during the synthesis or extension of the newly synthesized DNA molecule may result in one or a number of mismatched base pairs. Thus, the synthesized DNA molecule need not be exactly complementary to the DNA template.

Incorporating. The term "incorporating" as used herein means becoming a part of a DNA molecule or primer.

Vector. A plasmid or phage DNA or other DNA sequence into which DNA may be inserted to be cloned. The vector may replicate autonomously in a host cell, and may be further characterized by one or a small number of endonuclease recognition sites at which such DNA sequences may be cut in a determinable fashion and into which DNA may be inserted. The vector may further contain a marker suitable for use in the identification of cells transformed with the vector. Markers, for example, are tetracycline resistance or ampicillin resistance. The words "cloning vehicle" are sometimes used for "vector."

Operably linked. As used herein means that the promoter controls the initiation of the expression of the polypeptide encoded by the structural gene.

Expression. Expression is the process by which a polypeptide is produced from a structural gene. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moleties may alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Fragment. A "fragment" of a molecule such as a protein or nucleic acid is meant to refer to any portion of the amino acid or nucleotide genetic sequence.

Variant. A "variant" of a protein or nucleic acid is meant to refer to a molecule substantially similar in structure and biological activity to either the protein or nucleic acid, or to a fragment thereof. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Analog. An "analog" of a protein or genetic sequence is meant to refer to a protein or genetic sequence substantially similar in function to a protein or genetic sequence described herein.

Allele. An "allele" is an alternative form of a gene occupying a given locus on the chromosome.

*Mutation.* A "mutation" is any detectable change in the genetic material which may be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells. A mutation may be any (or a combination of) detectable, unnatural change affecting the chemical or physical constitution, mutability, replication, phenotypic function, or recombination of one or more deoxyribonucleotides; nucleotides may be added, deleted, substituted for, inverted, or transposed to new positions with and without inversion. Mutations may occur spontaneously and can be induced experimentally by application of mutagens. A mutant variation of a nucleic acid molecule results from a mutation. A mutant polypeptide may result from a mutant nucleic acid molecule.

Species. A "species" is a group of actually or potentially interbreeding natural populations. A species variation within a nucleic acid molecule or protein is a change in the nucleic acid or amino acid sequence that occurs among species and may be determined by DNA sequencing of the molecule in question.

Recombinant host. Any prokaryotic or eukaryotic or microorganism which contains the desired cloned genes on an expression vector, cloning vector or any DNA molecule. The term "recombinant host" is also meant to include those host cells which have been genetically engineered to contain the desired gene on the host chromosome or genome.

Host. Any prokaryotic or eukaryotic microorganism that is the recipient of a replicable expression vector, cloning vector or any DNA molecule. The DNA molecule may contain, but is not limited to, a structural gene, a promoter and/or an origin of replication.

Substantially Pure. As used herein "substantially pure" means that the desired purified protein or nucleic acid is essentially free from contaminating cellular contaminants which are associated with the desired protein or nucleic acid in nature as evidenced, for example, as one band on an electrophorectic gel. Contaminating cellular components may include, but are not limited to, phosphatases, exonucleases, endonucleases or undesirable DNA polymerase enzymes.

Thermostable. As used herein "thermostable" refers to a DNA polymerase which is resistant to inactivation by heat. DNA polymerases synthesize the formation of a DNA molecule complementary to a single-stranded DNA template by extending a primer in the 5' to 3' direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable DNA polymerase activity is more resistant to heat inactivation than a mesophilic DNA polymerase. However, a thermostable DNA polymerase does not mean to refer to an enzyme which is totally resistant to heat inactivation and thus heat treatment may reduce the DNA polymerase activity to some extent. A thermostable DNA polymerase typically will also have a higher optimum temperature than mesophilic DNA polymerases. Preferably, the thermostable DNA polymerase will lose substantially no activity after 60 minutes at 95° C.

DESCRIPTION OF THE PREFERRED EMBODIMENTS

For purposes of clarity of disclosure, and not by way of limitation, the detailed description of the invention is divided into the following subsections:

I. Isolated nucleic acid molecules coding for the DNA polymerase, and fragments thereof.

II. Substantially pure DNA polymerase.

III. DNA polymerases which lack the 3'–5' exonuclease activity.

IV. Kits containing the DNA polymerase.

V. A nucleic acid probe for the detection of the DNA polymerase nucleic acid.

VI. A method of detecting the presence of the DNA polymerase nucleic acid in a sample.

VII. DNA constructs comprising a DNA polymerase nucleic acid molecule and cells containing these constructs.

VIII. An antibody having binding affinity to the DNA polymerase, or a binding fragment thereof and a hybridoma containing the antibody.

IX. A method for purifying thermostable proteins.

I. Isolated Nucleic Acid Molecules Coding for the DNA Polymerase, and Fragments Thereof.

In one embodiment, the present invention relates to an isolated nucleic acid molecule coding for a DNA polymerase comprising amino acids 99 to 135 set forth in SEQ ID NO:2, or at least 39 contiguous amino acids thereof (preferably, at least 50, 70, or 100 contiguous amino acids thereof). In one preferred embodiment, the nucleic acid molecule codes for a DNA polymerase comprising amino acids 98 to 136 set forth in SEQ ID NO:2. In another preferred embodiment, the isolated nucleic acid molecule comprises the sequence set forth in SEQ ID NO:1; allelic, mutant or species variation thereof, or at least 20 contiguous nucleotides thereof (preferably at least 25, 30, 35, 40, or 50 contiguous nucleotides thereof). In another preferred embodiment, the isolated nucleic acid molecule encodes the amino acid sequence set forth in SEQ ID NO:2, or mutant or species variation thereof, or at least 39 contiguous amino acids thereof (preferably, at least 50, 70, or 100 contiguous amino acids thereof).

In another preferred embodiment, the nucleic acid molecule is greater than 80% homologous to the sequences set forth in SEQ ID NO:1; allelic, mutant or species variation thereof, or at least 20 contiguous nucleotides thereof (preferably at least 25, 30, 35, 40, or 50 contiguous nucleotides thereof). In another preferred embodiment, the nucleic acid molecule is greater than 90% homologous. In yet another preferred embodiment, the nucleic acid molecule is greater than 95% homologous. Homologous nucleic acid molecules may be identified using hybrididdation conditions (prefereably, stringent hybridization conditions) as described in Sambrook et al., In: *Molecular Cloning, A Laboratory Manual,* Cold Spring Harbor Laboratory Press, Cold Spring Harbor, N.Y.(1989).

Also included within the scope of this invention are the functional equivalents of the herein-described isolated nucleic acid molecules and derivatives thereof. The DNA polymerase and nucleic acid of the invention can be isolated from any strain of Desulfurococcus which produces a DNA polymerase having the molecular weight of 95 kilodaltons. The preferred strain to isolate the gene encoding the DNA polymerase of the present invention is Desulfurococcus strain Tok12-S1 obtained from Pacific Enzymes Ltd., Aukland, New Zealand (now, UniServices).

Additionally, the nucleic acid sequences depicted in SEQ ID NO: 1 can be altered by substitutions, additions or deletions that provide for functionally equivalent molecules. Due to the degeneracy of nucleotide coding sequences, other DNA sequences which encode substantially the same amino acid sequence as depicted in SEQ ID NO:2 may be used in the practice of the present invention. These include but are not limited to nucleotide sequences comprising all or portions of the DNA polymerase nucleic acid depicted in SEQ ID NO: 1 which are altered by the substitution of different codons that encode a functionally equivalent amino acid residue within the sequence, thus producing a silent change.

Such functional alterations of a given nucleic acid sequence afford an opportunity to promote secretion and/or processing of heterologous proteins encoded by foreign nucleic acid sequences fused thereto. All variations of the nucleotide sequence of the DNA polymerase genes and fragments thereof permitted by the genetic code are, therefore, included in this invention.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the present nucleic acid sequence or its derivative, or from the addition of TAA, TAG or TGA as a termination codon at the 3'-end of the inventive nucleotide sequence or its derivative.

Moreover, the nucleic acid molecule of the present invention may, as necessary, have restriction endonuclease recognition sites added to its 5'-end and/or 3'-end.

Further, it is possible to delete codons or to substitute one or more codons by codons other than degenerate codons to produce a structurally modified polymerase, but one which has substantially the same utility or activity of the polymerase produced by the unmodified nucleic acid molecule. As recognized in the art, the two polymerases are functionally equivalent, as are the two nucleic acid molecules which give rise to their production, even though the differences between the nucleic acid molecules are not related to degeneracy of the genetic code.

A. Isolation of Nucleic Acid.

In one aspect of the present invention, isolated nucleic acid molecules coding for polypeptides having amino acid sequences corresponding to the above-described DNA polymerase are provided. In particular, the nucleic acid molecule may be isolated from a biological sample containing RNA or DNA.

The nucleic acid molecule may be isolated from a biological sample containing RNA using the techniques of cDNA cloning and subtractive hybridization. The nucleic acid molecule may also be isolated from a cDNA library using a homologous probe.

The nucleic acid molecule may be isolated from a biological sample containing genomic DNA or from a genomic library using techniques well known in the art. The method of obtaining the biological sample will vary depending upon the nature of the sample.

One skilled in the art will realize that the genome of an organism may be subject to slight allelic variations between individuals. Therefore, the isolated nucleic acid molecule is also intended to include allelic variations, so long as the sequence is a functional derivative of the DNA polymerase gene. When an allele does not encode the identical sequence to that of SEQ ID NO: 1, it can be isolated and identified as the DNA polymerase using the same techniques used herein, and especially PCR techniques to amplify the appropriate gene with primers based on the sequences disclosed herein.

One skilled in the art will realize that organisms other than Desulfurococcus will also contain genes similar to the Desulfurococcus strain Tok12-S1 DNA polymerase gene (for example Thermococcus strain AN1 (DSM 2770)). The invention is intended to include, but not be limited to, the DNA polymerase nucleic acid molecules isolated from the above-described organisms.

B. Synthesis of Nucleic Acid.

Isolated nucleic acid molecules of the present invention are also meant to include those chemically synthesized. For example, a nucleic acid molecule with the nucleotide sequence which codes for the expression product of the DNA polymerase gene may be designed and, if necessary, divided into appropriate smaller fragments. Then an oligomer which corresponds to the nucleic acid molecule, or to each of the divided fragments, may be synthesized. Such synthetic oligonucleotides may be prepared, for example, by the triester method of Matteucci et al., *J. Am. Chem. Soc.* 103:3185–3191 (1981) or by using an automated DNA synthesizer.

An oligonucleotide may be derived synthetically or by cloning. If necessary, the 5'-ends of the oligomers may be phosphorylated using T4 polynucleotide kinase. Kinasing of single strands prior to annealing or for labeling may be achieved using an excess of the enzyme. If kinasing is for the labeling of probe, the ATP may contain high specific activity radioisotopes. Then, the DNA oligomer may be subjected to annealing and ligation with T4 ligase or the like.

II. Substantially Pure DNA Polymerase Polypeptides.

In another embodiment, the present invention relates to a substantially pure DNA polymerase comprising amino acids 99 to 135 set forth in SEQ ID NO:2, or a fragment or derivative thereof, or at least 39 contiguous amino acids thereof (preferably, at least 50, 70, or 100 contiguous amino acids thereof), or a functional derivative thereof. In a preferred embodiment, the polymerase comprises amino acids 98 to 136 set forth in SEQ ID NO:2. In another preferred embodiment, the polypeptide has the amino acid sequence set forth in SEQ ID NO:2, or mutant or species variation thereof, or at least 39 contiguous amino acids thereof (preferably, at least 50, 70, or 100 contiguous amino acids thereof).

Amino acid sequence variants of the DNA polymerase can be prepared by mutations in the DNA. Such variants include, for example, deletions from, or insertions or substitutions of, residues within the amino acid sequence shown in SEQ ID NO:2. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

While the site for introducing an amino acid sequence variation is predetermined, the mutation per se need not be predetermined. For example, to optimize the performance of a mutation at a given site, random mutagenesis may be conducted at the target codon or region and the expressed DNA polymerase variants screened for the optimal combination of desired activity. Techniques for making substitution mutations at predetermined sites in DNA having a known sequence are well known and include, for example, site-specific mutagenesis.

Preparation of a DNA polymerase variant in accordance herewith is preferably achieved by site-specific mutagenesis of DNA that encodes an earlier prepared variant or a nonvariant version of the protein. Site-specific mutagenesis allows the production of DNA polymerase variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Vieira et al., *Meth. Enzymol.* 153:3 (1987)) may be employed to obtain single-stranded DNA.

In general, site-directed mutagenesis in accordance herewith is performed by the technique described by Kunkel,

*Proc. Natl. Acad. Sci.* 82:488–492 (1985). An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded DNA obtained from *E. coli* CJ236 (Kunkel, et al., *Proc. Natl. Acad. Sci.* 154:367–382 (1987)) and subjected to DNA-polymerizing enzymes such as T4 DNA polymerase, T7 DNA polymerase, or *E. coli* polymerase I Klenow fragment, to complete the synthesis of the mutation-bearing strand. Thus, a mutated sequence and the second strand bears the desired mutation. This heteroduplex vector is then used to transform appropriate cells such as DH5αF'$I^q$ , cells (Life Tech. Inc.) and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host. A PCR directed mutagenesis can also be performed to obtain similar clones.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete DNA polymerase sequence) may range generally from about 1 to 10 residues, more preferably 1 to 5. An example of a terminal insertion includes a fusion of a signal sequence, whether heterologous or homologous to the host cell, to the N-terminus of the DNA polymerase to facilitate the secretion of DNA polymerase from recombinant hosts.

The third group of variants are those in which at least one amino acid residue in the DNA polymerase molecule, and preferably, only one, has been removed and a different residue inserted in its place. Such substitutions preferably are made in accordance with the following Table 1 when it is desired to modulate finely the characteristics of the DNA polymerase.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to cause the above changes are those in which (a) glycine and/or proline is substituted by another amino acid or is deleted or inserted; (b)a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of the DNA polymerase. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native DNA polymerase encoding-nucleic acid, expression of the variant nucleic acid in recombinant cell culture and, optionally, purification from the cell culture, for example, by immunoaffinity adsorption on a column (to absorb the variant by binding it to at least one remaining immune epitope). The activity of the cell lysate or purified DNA polymerase molecule variant is then screened in a suitable screening assay for the desired characteristic. For example, a change in the immunological character of the DNA polymerase molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from cells which naturally produce the peptide. Alternatively, the above-described isolated nucleic acid fragments could be used to expressed the DNA polymerase in any organism. The samples of the present invention include cells, protein extracts or membrane extracts of cells, or biological fluids. The sample will vary based on the assay format, the detection method and the nature of the cells or extracts used as the sample.

Any organism can be used as a source for the polymerase of the invention, as long as the source organism naturally contains such a polymerase. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromotography, size-exclusion chromatography, HPLC, ion-exchange chromatography, and immuno-affinity chromatography.

III. DNA Polymerases Which Lack the 3'–5' Exonuclease Activity.

The DNA polymerase of the invention can be modified such that the polymerase lacks the 3'–5' exonuclease activity.

A comparison of the amino acid sequence with other known DNA polymerases such as DNA polymerase I (*Science* 240:199–201 (1988)), ϕ29 (*Cell* 59:219–228 (1989)) and T5 DNA polymerase (U.S. Pat. No. 5,270,179) revealed potential amino acids implicated to be associated with 3'–5' activity. These amino acids are Asp(D) at amino acid 141 and Glu(E) at amino acid 143.

The region of the polymerase which contains the exonuclease activity may also be identified by site specific mutation, random mutation or deletion.

Mutation of the polymerase can be achieved as described above. Preferably, a DNA fragment encoding the polymerase is mutated. The fragment is then expressed and the cells expressing the polymerase are assayed for polymerase and exonuclease activity.

The DNA polymerases described above which lack the 3'–5' exonuclease activity may be used in well known DNA sequencing, DNA labeling, and DNA amplification reactions. As is well known, sequencing reactions (dideoxy DNA sequencing and cycle DNA sequencing of plasmid DNA) require the use of DNA polymerases. Dideoxy-mediated sequencing involves the use of a chain-termination technique which uses a specific polymer for extension by DNA polymerase, a base-specific chain terminator and the use of polyacrylamide gels to separate the newly synthesized chain-terminated DNA molecules by size so that at least a part of the nucleotide sequence of the original DNA molecule can be determined. Specifically, a DNA molecule is sequenced by using four separate DNA sequence reactions, each of which contains different base-specific terminators. For example, the first reaction will contain a G-specific terminator, the second reaction will contain a T-specific terminator, the third reaction will contain an A-specific terminator, and a fourth reaction may contain a C-specific terminator. Preferred terminator nucleotides include dideoxyribonucleoside triphosphates (ddNTPs) such as ddATT, ddTPP, ddGPP, and ddCPP. Analogs of dideoxyribonucleoside triphosphates may also be used and are well known in the art.

When sequencing a DNA molecule, ddNTPs lack a hydroxyl residue at the 3' position of the deoxyribose base and thus, although they can be incorporated by DNA polymerases into the growing DNA chain, the absence of the 3'-hydroxy residue prevents formation of a phosphodiester bond resulting in termination of extension of the DNA molecule. Thus, when a small amount of one ddNTP is included in a sequencing reaction mixture, there is competition between extension of the chain and base-specific termination resulting in a population of synthesized DNA molecules which are shorter in length than the DNA template to be sequenced. By using four different ddNTPs in four separate enzymatic reactions, populations of the synthesized DNA molecules can be separated by size so that at least a part of the nucleotide sequence of the original DNA molecule can be determined. DNA sequencing by dideoxynucleotides is well known and is described by Sambrook et al., In: *Molecular Cloning, A Laboratory Manual,* Cold Spring Harbor Laboratory Press, Cold Spring Harbor, N.Y. (1989). As will be readily recognized, the DNA polymerase of the present invention may be used in such sequencing reaction.

As is well known, detectably labeled nucleotides are typically included in sequencing reactions. Any number of labeled nucleotides can be used in sequencing (or labeling) reactions, including, but not limited to, radioactive isotopes, fluorescent labels, chemiluminescent labels, bioluminescent labels, and enzyme labels. The DNA polymerases which lack the 3'–5' exonuclease activity may be particularly useful for incorporating αS nucleotides (dATPαS, dTTPαS, dCTPαS and dGTPαS) during sequencing (or labeling) reactions.

Polymerase chain reaction (PCR), a well known DNA amplification technique, is a process by which DNA polymerase and deoxyribonucleoside triphosphates are used to amplify a target DNA template. In such PCR reactions, two primers, one complementary to the 3' termini (or near the 3' termini) of the first strand of the DNA molecule to be amplified, and a second primer complementary to the 3' termini (or near the 3' termini) of the second strand of the DNA molecule to be amplified, are hybridized to their respective DNA molecules. After hybridization, DNA polymerase, in the presence of deoxyribonucleoside triphosphates, allows the synthesis of a third DNA molecule complementary to the first strand and a fourth DNA molecule complementary to the second strand of the DNA molecule to be amplified. This synthesis results in two double stranded DNA molecules. Such double stranded DNA molecules may then be used as DNA templates for synthesis of additional DNA molecules by providing a DNA polymerase, primers, and deoxyribonucleoside triphosphates. As is well known, the additional synthesis is carried out by "cycling" the original reaction (with excess primers and deoxyribonucleoside triphosphates) allowing multiple denaturing and synthesis steps. Typically, denaturing of double stranded DNA molecules to form single stranded DNA templates is accomplished by high temperatures.

DNA polymerases which lack the 3'–5' exonuclease activity are ideally suited for PCR reactions, particularly where high temperatures are used to denature the DNA molecules during amplification.

IV. Kits Containing The DNA Polymerase

The DNA polymerases described above (with or without the exonuclease) are ideally suited for the preparation of a kit. Kits comprising certain DNA polymerases may be used for detectably labeling DNA molecules, DNA sequencing, or amplifying DNA molecules by well known techniques, depending on the content of the kit. Such kits may comprise a carrying means being compartmentalized to receive in close confinement therein one or more container means such as vials, test tubes and the like. Each of such container means comprises components or a mixture of components needed to perform DNA sequencing, DNA labeling, or DNA amplification.

A kit for sequencing DNA may comprise a number of container means. A first container means may, for example, comprise a substantially purified sample of the DNA polymerase having the molecular weight of about 95 kilodaltons. A second container means may comprise one or a number of types of nucleotides needed to synthesize a DNA molecule complementary to DNA template. A third container means may comprise one or a number different types of dideoxynucleoside triphosphates. In addition to the above container means, additional container means may be included in the kit which comprise one or a number of DNA primers.

A kit used for amplifying DNA will comprise, for example, a first container means comprising the substantially pure DNA polymerase and one or a number of additional container means which comprise a single type of nucleotide or mixtures of nucleotides. Various primers may or may not be included in a kit for amplifying DNA.

When desired, the kit of the present invention may also include container means which comprise detectably labeled nucleotides which may be used during the synthesis or sequencing of a DNA molecule. One of a number of labels may be used to detect such nucleotides. Illustrative labels include, but are not limited to, radioactive isotopes, fluorescent labels, chemiluminescent labels, bioluminescent labels and enzyme labels.

V. A Nucleic Acid Probe For The Detection Of DNA Polymerase Nucleic Acid.

In another embodiment, the present invention relates to a nucleic acid probe for the detection of the presence of the above-described DNA polymerase in a sample comprising the above-described nucleic acid molecules or at least 20 contiguous nucleotides thereof (preferably at least 25, 30, 35, 40, or 50 thereof). In another preferred embodiment, the nucleic acid probe has the nucleic acid sequence set forth in SEQ ID NO:1 or at least 20 contiguous nucleotides thereof (preferably at least 25, 30, 35, 40, or 50 thereof). In another preferred embodiment, the nucleic acid probe encodes the amino acid sequence set forth in SEQ ID NO:2 or at least 39 contiguous amino acids thereof.

In another embodiment, the present invention provides for nucleic acid probes comprising a nucleic acid molecule which is capable of hybridizing to the DNA polymerase nucleic acid (preferably, the sequence of the nucleic acid is substantially the same as that depicted in SEQ ID NO: 1 or portions thereof of that are at least 20 nucleotides).

The nucleic acid probe may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. *Molecular Cloning: A Laboratory Manual, second edition,* edited by Sambrook, Fritsch, & Maniatis, Cold Spring Harbor Laboratory, 1989).

In the alternative, chemical synthesis is carried out in order to obtain nucleic acid primers having nucleotide sequences which correspond to N-terminal portion and the complement of C-terminal portion of the amino acid sequence of the polypeptide of interest. Thus, the synthesized nucleic acid probes may be used as primers in a polymerase chain reaction (PCR) carried out in accordance with recognized PCR techniques, essentially according to *PCR Protocols, A Guide to Methods and Applications,* edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. *Molecular Cloning: A Laboratory Manual, second edition,* edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleie acid extracts of cells are well known in the art and can be readily adapted in order to obtain a sample which is compatible with the method utilized.

VI. A Method Of Detecting The Presence Of The DNA Polymerase Nucleic Acid In A Sample.

In another embodiment, the present invention relates to a method of detecting the presence of the DNA polymerase nucleic acid in a sample comprising a) contacting the sample with the above-described nucleic acid probe, under conditions such that hybridization occurs, and b) detecting the presence of the probe bound to the nucleic acid molecule. One skilled in the art would select the nucleic acid probe according to techniques known in the art as described above.

VII. DNA Constructs Comprising A DNA Polymerase Nucleic Acid Molecule and Cells Containing These Constructs.

In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecules.

In another embodiment, the present invention relates to a nucleic acid molecule comprising a transcriptional region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotie cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a DNA polymerase gene may be obtained by the above-described methods. Where the transcriptional termination signals are not satisfactorily functional in the expression host cell, then a 3' region functional in the host cell may be substituted.

Two DNA sequences (such as a promoter region sequence and a DNA polymerase gene sequence) are said to be operably linked if the nature of the linkage between the two DNA sequences does not (1) result in the introduction of a frame-shift mutation, (2) interfere with the ability of the promoter region sequence to direct the transcription of a DNA polymerase gene sequence, or (3) interfere with the ability of the a DNA polymerase gene sequence to be transcribed by the promoter region sequence. Thus, a promoter region would be operably linked to a DNA sequence if the promoter were capable of effecting transcription of that DNA sequence.

The present invention encompasses the expression of the DNA polymerase gene (or a functional derivative thereof) in either prokaryotic or eukaryotic cells. Prokaryotic hosts are, generally, the most efficient and convenient for the production of recombinant proteins and, therefore, are preferred for the expression of the DNA polymerase gene.

Prokaryotes most frequently are represented by various strains of *E. coli.* However, other microbial strains may also be used, including other bacterial strains. In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

A preferred host for cloning the DNA polymerase gene of the invention is a prokaryotic host. The most preferred prokaryotic host is *E. coli.* However, the DNA polymerase gene of the present invention may be cloned in other prokaryotic hosts including, but not limited to, Escherichia, Bacillus, Streptomyces, Pseudomonas, Salmonella, Serratia, and Proteus. Bacterial hosts of particular interest include *E. coli* DH10B, which may be obtained from Life Technologies, Inc., (Gaithersburg, Maryland).

To express the DNA polymerase (or a functional derivative thereof) in a prokaryotic cell, it is necessary to operably link the DNA polymerase sequence to a functional prokaryotic promoter. Such promoters may be either constitutive or, more preferably, regulatable (i.e., inducible or derepressible). Examples of constitutive promoters include the int promoter of bacteriophage λ, the bla promoter of the βlactamase gene sequence of pBR322, and the CAT promoter of the chloramphenicol acetyl transferase gene sequence of pBR325, and the like. Examples of inducible prokaryotic promoters include the major right and left promoters of bacteriophage λ ($P_L$ and $P_R$), the trp, recA, lacZ, lacI, and gal promoters of *E. coli,* the α-amylase (Ulmanen et al., *J. Bacteriol.* 162:176–182 (1985)) and the delta-28-specific promoters of *B. subtilis* (Gilman et al., *Gene sequence* 32:11–20 (1984)), the promoters of the bacteriophages of Bacillus (Gryczan, In: *The Molecular Biology of the Bacilli,* Academic Press, Inc., NY (1982)), and Streptomyces promoters (Ward et al., *Mol. Gen. Genet.* 203:468–478 (1986)). Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

The selection of control sequences, expression vectors, transformation methods, and the like, are dependent on the type of host cell used to express the gene. As used herein, "cell," "cell line," and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the DNA polymerase of interest. Suitable hosts may often include eukaryotic cells.

Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example Drosophila larvae. Using insect cells as hosts, the Drosophila alcohol dehydrogenase promoter can be used. Rubin, *Science* 240:1453–1459 (1988). Alternatively, baculovirus vectors can be engineered to express large amounts of the DNA polymerase in insects cells (Jasny, *Science* 238:1653 (1987); Miller et al., In: *Genetic Engineering* (1986), Setlow, J. K., et al., eds., *Plenum,* Vol. 8, pp. 277–297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous DNA polymerase protein. Furthermore, different vector/host expression systems may effect processing reactions such as proteolytic cleavages to different extents.

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out posttranslational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of the DNA polymerase.

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of the DNA polymerase in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature (London)* 290:304–310 (1981)); the yeast gal4 gene sequence promoter (Johnston et al., *Proc. Natl. Acad. Sci. (USA)* 79:6971–6975 (1982); Silver et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the DNA polymerase (or a functional derivative thereof) does not contain any intervening codons which are capable of encoding a methionine (i.e., AUG). The presence of such codons results either in a formation of a fusion protein (if the AUG codon is in the same reading frame as the DNA polymerase coding sequence) or a frame-shift mutation (if the AUG codon is not in the same reading frame as the DNA polymerase coding sequence).

A DNA polymerase nucleic acid molecule and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or vital vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual,* second edition, edited by Sambrook, Fritsch, & Maniatis, Cold Spring Harbor Laboratory, 1989)). Bacillus plasmids include pC194, pC221, pT127, and the like. Such plasmids are disclosed by Gryczan (In: *The Molecular Biology of the Bacilli,* Academic Press, N.Y. (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology,* Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance,* Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise,* Vol. 3, Gene Sequence Expression, Academic Press, N.Y., pp. 563–608 (1980)).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of the DNA polymerase or fragments thereof. This can take place in the transformed cells as such, or following the induction of these cells to differentiate (for example, by administration of bromodeoxyuracil to neuroblastoma cells or the like).

The polymerases of the present invention (DNA polymerases) are preferably produced by fermentation of the recombinant host containing and expressing the cloned DNA polymerase gene. However, the DNA polymerase of the present invention may be isolated from any strain which produces the polymerase of the present invention.

Any nutrient that can be assimilated by a host containing the native or cloned DNA polymerase gene may be added to the culture medium. Optimal culture conditions should be selected case by case according to the strain used and the composition of the culture medium. Antibiotics may also be added to the growth media to insure maintenance of vector DNA containing the desired gene to be expressed. Culture conditions for Desulfurococcus strain Tok12-S 1 have, for example, been described by Cowan et al., *Biochem, J.* 247:121–133 (1987). Media formulations are also described by Finegold et al., In: *Diagnostic Microbiology* (5th ed.), The C.V. Mosby Company, St. Louis, Mich. (1978) and Sambrook et al., In: *Molecular Cloning, A Laboratory Manual* (2nd ed.), Cold Spring Harbor Laboratory Press, Cold Spring Harbor, N.Y. (1989).

Native and recombinant host cells producing the DNA polymerase of this invention can be separated from liquid culture, for example, by centrifugation. In general, the collected microbial cells are dispersed in a suitable buffer, and then broken down by ultrasonic treatment or by other well known procedures to allow extraction of the polymerases by the buffer solution. After removal of cell debris by ultracentrifugation or centrifugation, the DNA polymerase can be purified by standard protein purification techniques such as extraction, precipitation, chromatography, affinity chromatography, electrophoresis or the like. Assays to detect the presence of the DNA polymerase during purification are well known in the art and can be used during conventional biochemical purification methods to determine the presence of these enzymes.

VIII. An Antibody Having Binding Affinity To The DNA Polymerase, Or A Binding Fragment Thereof And A Hybridoma Containing The Antibody.

In another embodiment, the present invention relates to an antibody having binding affinity to the DNA polymerase, or a binding fragment thereof. In a preferred embodiment, the polypeptide has the amino acid sequence set forth in SEQ ID NO:2, or mutant or species variation thereof, or at least 39 contiguous amino acids thereof (preferably, at least 40, 50, or 100 contiguous amino acids thereof).

In another preferred embodiment, the present invention relates to an antibody having binding affinity to the DNA polymerase, or a binding fragment thereof. Those which bind selectively to the DNA polymerase would be chosen for use in methods which could include, but should not be limited to, the analysis of altered DNA polymerase expression in tissue containing the DNA polymerase.

The DNA polymerase peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well fragments of these antibodies. Antibody fragments which contain the idiotype of the molecule can be generated by known techniques. For example, such fragments include but are not limited to: the $F(ab')_2$ fragment; the Fab' fragments, and the Fab fragments.

In another embodiment, the present invention relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide in a suitable vehicle. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology,* supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide,* W. H. Freeman, N.Y., pp. 289–307 (1992), and Kaspczak et al., *Biochemistry* 28:9230–8 (1989).

IX. A Method For Purifying Thermostable Proteins.

In another embodiment, the present invention relates to a method for purifying thermostable proteins. More specifically, the method for purifying thermostable proteins (preferably, proteins larger than 50 kd in size, more specifically, thermostable DNA polymerases) comprises heating a sample above 70° C. containing the thermostable protein and then, purifying the thermostable proteins by gel filtration.

The method is based on the unexpected discovery that heating an aqueous *E. coli* extract differentially precipitates large *E. coli* proteins having molecular weights similar to DNA polymerase. Therefore, the cloned DNA polymerase is predominantly contaminated with smaller *E. coli* proteins. After heating, the thermostable proteins are easily purified by methods well known in the art, for example, by using gel filtration columns.

In one preferred embodiment, the DNA polymerase of the present invention is purified by heating *E. coli* extracts at 75° C. for 30 min. and then purifying the soluble proteins further with gel filtration.

Having now generally described the invention, the same will be more readily understood through reference to the following Examples which are provided by way of illustration, and are not intended to be limiting of the present invention, unless specified.

EXAMPLE 1

Bacterial Strains And Growth Conditions

Desulfurococcus strain Tok12-S1 cell paste was obtained from PEL (Pacific Enzymes Limited, Aukland, New Zealand)(Patel et al., *New Zealand J. Marine Freshwater Res.* 20:439–445 (1986)). *E. coli* strain DH10B (Life Technologies, Inc., Gaithersburg, Md.) and CJ374 (Cathy Joyce, Yale University) were used as host strains.

*E. coli* strains were grown in 2X LB broth base (Lennox L broth base: GIBCO/BRL) medium. Transformed cells were incubated in SOC (2% tryptone, 0.5 % yeast extract, 10 mM NaCl, 2.5M KC1, 20 mM KCl, 20 mM glucose, 10 mM $MgCl_2$, and 10 mM $MgSO_4$ per liter) before plating. When appropriate, antibiotic supplements were 100 micrograms/ml ampicillin, 50 micrograms/ml kanamycin, 30 micrograms/ml chloramphenicol.

EXAMPLE 2

DNA Isolation

Desulfurococcus chromosomal DNA was isolated from 1.1 g of cells suspended in 2.5 ml of TNE buffer (50 mM Tris-HCl, pH8.0, 50 mM NaCl, 10 mM EDTA) and treated with 1% SDS for 10 minutes at 37° C. DNA was extracted with phenol by gently rocking the lysed cells overnight at 4 ° C. The 2O aqueous layer was extracted with chloroform: isoamyl alcohol. The resulting chromosomal DNA was further purified by centrifugation in a CsCl density gradient. Chromosomal DNA isolated from the density gradient was extracted three times with 20X SSC saturated isopropanol and dialyzed overnight against a buffer containing 10 mM Tris-HCl, pH 8.0 and 1 mM EDTA.

EXAMPLE 3

Screening for Clones Expressing Desulfurococcus DNA Polymerase

The Polymerase Chain Reaction (PCR) is a powerful technique for amplifying regions from small quantities of DNA. Specific deoxyoligonucleotides can be utilized in this reaction to obtain DNA sizes of predicted length. The known amino acid sequences of DNA polymerases contain many conserved homologous regions. Degenerate deoxyoligonucleotides were designed to anneal in 2 of these regions of conserved homology to generate a specific PCR product of about 600 bp. The PCR product may be sequenced to confirm that it was generated from DNA polymerase sequences. The same PCR product may also be used as a probe to hybridize to the Desulfurococcus chromosomal DNA in order to obtain the remainder of the polymerase gene. The forward primer (1906) 26 nucleotides and the reverse primer (1910) 31 nucleotides are listed below:

Forward Primer (1906)(SEQ ID NO:3)

5'CG ATC <u>TCT AGA</u> (A/G)AG AGA (A/G)AT GAT AAA G 3'

Reverse Primer (1910)(SEQ ID NO:4)

5' CG ATC <u>GGA TCC</u> CAC AA(A/C) CC(T/C) TTT TCT GGC TC 3'

Both primers were designed to contain restriction sites near the 5' end for use in cloning the PCR product into a vector. The forward primer contains an XbaI site while the reverse primer contains a BamHI site. The 5' nine nucleotides of the forward primer and the 5' eight nucleotides of the reverse primer have no homology to the polymerase. The conditions used were as follows: 50ng of Desulfurococcus chromosomal DNA and 1 micromoles of forward and reverse primers were added to a PCR reaction and incubated using the following conditions: 1 cycle of 94° C. for 5 minutes, 2.5 units of Taq DNA polymerase (Perkin-Elmer, Cetus), 25 cycles were performed as follows: denaturation at 94° C., 30 seconds; primer annealing at 50° C., 30 seconds; and extension at 72° C., 2 minutes. The PCR reaction was purified by adding 1/10 volume 3M ammonium acetate and 2.5 volumes 95 % ethanol. The DNA was collected in 30 microliter of REact 2 (LTI) containing 15 units of XbaI and BamHI. The sample was incubated for 45 minutes at 37° C. and applied to an agarose gel. The 600 bp fragment was extracted from the gel and purified away from the agarose using a GeneClean Kit™ (BIO- 101, La Jolla, Calif.). A 10 microliter ligation reaction containing the purified PCR product, the vector pUC19 digested with XbaI and BamHI (purified as above), 1X ligase buffer (LTI), and 1 unit of T4 DNA ligase (LTI) was incubated for 1.5 hours at 22° C. Competent DH10B cells were transformed with 0.3 microliters of the ligation reaction mix. Transformants were selected on agar plates containing ampicillin incubated at 30° C. Plasmid DNA from four colonies was isolated and screened by miniprep DNA analysis to determine if the clones contained the 600bp PCR product. Three of the four clones contained the desired insert. One of the clones was further analyzed by DNA sequence analysis and determined to contain a specific region of a DNA polymerase gene based upon the nucleic and amino acid homology to other known DNA polymerases.

EXAMPLE 4

Constructing the Intact DNA Polymerase Gene

The chromosomal DNA isolated in Example 2 was used to construct a genomic library in the cosmid pCP13. Briefly, 100 micrograms of Desulfurococcus chromosomal DNA was partially digested with Sau3AI for 1 hour at 37° C. and then concentrated by EtOH precipitation. The partially digested chromosomal DNA was ligated into the cosmid pCP13 digested with BamHI and dephosphorylated with calf intestinal phosphatase. Ligation of the partially digested Desulfurococcus DNA and the BamHI cleaved pCP13 DNA was carried out with 1 unit of T4 DNA ligase at 22° C. for 18 hours. After ligation, a portion of the ligation reaction was packaged into lambda phage particles (Lambda Packaging Kit obtained from Life Technologies, Inc., Gaithersburg, Md.) and used to infect DH10B cells. Infected cells were applied onto tetracycline containing plates. Approximately 3,000 tetracycline resistant colonies were obtained. Serial dilutions were made such that approximately 200 to 300 tetracycline resistant colonies were applied per plate.

EXAMPLE 5

Screening Clones Containing the DNA Polymerase

Identification of the Desulfurococcus DNA polymerase gene of the invention was cloned using the colony hybridization method described by Sambrook et al., in: Molecular Cloning, A Laboratory Manual, Cold Spring Harbor Laboratory Press, Cold Spring Harbor, N.Y.(1989). The tetracycline resistant colonies from Example 4 were transferred to nylon support membranes and processed for colony hybridization as described: Briefly, the filters were treated with 10% SDS (sodium dodecylsulfate) followed by treatment with 0.5M NaOH, 1.0M NaCl for 5 minutes; then 0.5M Tris-HCl (pH 8.0), 1.5M NaCl for 5 minutes; and 6X SSC for 5 minutes. The filters were air dried and baked in a vacuum oven for 1 hour at 80° C. The filters were then probed with a 32P random primer labelled 600 bp Desulfurococcus polymerase gene fragment described in Example 3. The DNA from colonies eliciting a signal were isolated and characterized by Southern Blot analysis and comparing DNA sequence to other known DNA polymerases. Analysis of the sequence homology data revealed the presence of two intervening sequences in the Desulfurococcus DNA polymerase gene. The intervening sequences were removed and the resulting Desulfurococcus DNA polymerase gene was cloned into an expression vector. Briefly, an NdeI site was created by PCR to include the initiation codon of the polymerase gene within the NdeI site. Restriction sites were also generated at the intervening sequence junctions by PCR. These restriction sites were designed to contain compatible ends such that when the pieces were joined together it would generate an in-frame Desulfurococcus DNA polymerase gene without intervening sequences. The intact gene was then cloned in pRE1, under control of the pL promoter. The resulting plasmid was used to transform competent CJ374. The transformants were selected on ampicillin and chloramphenicol plates. The colonies were screened by plasmid DNA restriction analysis and the positive clones were then assayed for heat-stable polymerase activity.

Specific Information Concerning the Cloning of the Intact Polymerase

The DNA from three separate PCR reactions were ligated to each other such that the intervening sequences were eliminated from the resulting clone. The two oligos designed for first PCR reaction are as follows:

PCR I

#2258 Forward Primer (SEQ ID NO:5)

5'0 CUA CUA CUA CUA TAA CAT ATG ATC CTC GAT GCT GAC 3'

112348 Reverse Primer (SEQ ID NO:6)

5' CAU CAU CAU CAU G ACT GTT GCC CAA GAT CTT GAT 3'

The forward primer creates a NdeI site at the initiation codon of the polymerase gene, while the reverse primer includes a MscI site 7 base pairs away from the junction of the polymerase gene and the first intervening sequence. The strategy was to ligate the second PCR product to the first PCR product at the MscI site. The PCR reactions were carried out as described in Example 3 with the following exceptions: (1) where 25 cycles were use in Example 3, only 8 cycles were used to minimize the possibility of a misincorporated base pair, or (2) a portion of the PCR product was treated with uracil-D-glycosylase (LTI) and cloned into pAMP1 (LTI) to generate pBJS96. The 2 remaining PCR products were treated in a similar manner. The oligos for the remaining 2 PCR reactions are listed below and the restriction sites (underlined) utilized for cloning into pAMP1 to produce (PCR II=pBJS93; PCR III= pBJS107):

PCR II

1/2349 Forward Primer (SEQ ID NO:7)

5' CUA CUA CUA CAU TTG GCC AAC AGT TAT TAC GGC TAC TAC GCG TAC GCA 3'

#12296 Reverse Primer (SEQ ID NO:8)

5' CAU CAU CAU CAU ATC GAT ATC CGC GTA AAG CAC TTT 3'

PCR III

#2297 Forward Primer (SEQ ID NO:9)

5'CUA CUA CUA CUA ACT AGT ACT GAC GGT TFC TTT GCC AC 3'

#2263 Reverse Primer (SEQ ID NO:10)

5'CAU CAU CAU CAU TGA GAA TTC TTT AGC CTT ATT TIT 3'

| Primer # | Site |
|---|---|
| 2258 | NdeI |
| 2348 | MscI |
| 2349 | MscI |
| 2296 | EcoRV |
| 2297 | ScaI |
| 2264 | EcoRI |

The three separate PCR products were ligated together at the appropriate restriction sites to generate pBJS107. The remaining portion of the carboxyl terminus was cloned into the EcoRI site on a 1.5Kb fragment resulting in (pBJS103). The resulting construction contained the entire polymerase gene without the intervening sequences and was cloned into the expression vector pRE1 resulting in (pBJS108).

EXAMPLE 6

An Expression Vector with the DNA Polymerase Gene

DNA sequence was obtained from subclones of the cosmid clone DTOK/pCP13. The position of the methionine start codon and the intron/exon junctions were determined based on amino acid homology to other polymerases. PCR was then performed on the polymerase gene subclones to incorporate an NdeI site at the start methionine residue and other blunt end restriction sites at the intron/exon junctions. The PCR products were first cloned separately into pAMP1 (LTI) and then pieced together at the created restriction sites. The restriction sites introduced were site-specific changes in 25 the DNA in order to create the recognition sites but did not alter the amino acid sequence. The carboxyl end of the gene was cloned on an EcoRI fragment. Once the gene was fully assembled without the intervening sequences, the entire polymerase gene was cloned into the expression vector pREI (Reddy et al., *Nucl. Acids Res.* 17:10473–10488 (1989)). The resulting plasmid was named pBJS 108. pREI is an *E. coli* plasmid which contains the pL promoter from the *E. coli* bacteriophage lambda. Expression from the pL promoter can be regulated by the temperature sensitive mutant repressor cI857. Competent cells containing a plasmid carrying the cI857 repressor gene (CJ374, Cathy Joyce, Yale University) were transformed with the DTOK polymerase gene in the pREI vector. *E. coli* CJ374 containing pBJS108 was named *E. coli* BJS108.

EXAMPLE 7

Construction of 3'–5' Exonuclease Mutants of the Polymerase

The alignment of the DNA polymerase sequence with other known DNA polymerase sequences such as T4, *E. coli* PolI, T5 and T7 DNA polymerases (Braithwaite and Ito, *Nucleic Acids Res.* 21:787–802 (1993) and Blanco et al., *Gene* 112:139–144 (1992)) revealed several conserved amino acids at the 3'–5' exonuclease domain. The amino acids that are possibly responsible for this activity were identified as Asp141, Glu143, Asp215, Asp314, Tyr310. Alteration of any of these amino acids would either diminish or reduce the 3'–5' exonuclease activity. Alteration of the Asp141 and Glu143 to Ala141 and Ala143 has resulted in 10,000 fold lower level of 3'–5' exonuclease activity. The oligo used for the mutation was 5' GAC GAG GAG CTC AGG ATG CTC GCC TTC GCG ATC GCG ACG CTC TAC CAT 3' (SEQ ID NO: 11). The mutagenesis was done by PCR. However, one can utilize another well known technique called Kunkel mutagenesis (Kunkel, *Proc. Natl. Acad. Sci.* 82:488–492 (1985)) to obtain the same result. The alteration of the amino acids were confirmed by DNA sequence.

EXAMPLE 8

Partial Purification of the DNA Polymerase from Desulfurococcus strain Tok12-S1

1.3 g of Desulfurococcus strain Tok12-S 1 cells were thawed on ice and suspended in 2.75 ml sonication buffer (50 mM Tris, pH 7.5, 1.0 mM EDTA, 10 mM KCl, 10% sucrose, 10% glycerol, 0.05 % Tween-20, 0.05 % NP-40, 1.0 mM βME, and 1.0 mM PMSF). Lysis was effected with six 10 second bursts with a Heat Systems Ultrasonics Inc., model 375 sonicator. The suspension was clarified by centrifugation in a microfuge at maximum r.p.m. at 4° C. for 1 hour. The supernatant fraction was collected (FRI 3.5 ml) and applied to a previously equilibrated 1 ml HiTrap Blue column (Pharmacia). The column was washed until baseline $OD_{280}$ was achieved. Elution was effected with a linear 30 column volume gradient of buffer A (50 mM Tris, pH 7.5, 1.0 mM EDTA, 10% glycerol, 0.05 % Tween-20, 0.05 % NP-40, and 5.0 mM DTT or 1.0 mM βME) to buffer A and 2 M KC1. 500μl fractions were collected. Polymerase activity eluted as a single peak centered in fraction 46. The Desulfurococcus polymerase was purified 41-fold in 67 % yield to a specific activity of 409 u/mg. Fractions containing greater than 50% peak activity were pooled and concentrated with a Centricon-30 (Amicon).

EXAMPLE 9

Purification of the DNA Polymerase from *E. coli*

Five grams of *E. coli* cells expressing cloned Desulfurococcus DNA polymerase were lysed by sonication (3 thirty-second bursts with a microtip at the maximum setting with a Heat Systems Ultrasonics Inc., model 375 sonicator) in 20 ml of ice cold extraction buffer (50 mM Tris HCl, pH 7.5, 8% glycerol, 3 mM mercaptoethanol, 10 mM KCl, 1 mM EDTA, 0.5 mM PMSF, and 0.05% each of Tween-20 and NP-40). This was centrifuged at 17,000xg at 4° C. for 60 min. and the supernatant was heated to 75° C. for 30 min. in a water bath. Precipitated proteins were removed by centrifugation at 100,000xg for 60 min. The remaining protein (11 mg) was loaded on a 5 ml column of Hitrap Blue agarose (Pharmacia) equilibrated with buffer A (50 mM Tris HCl, pH 7.5, 8% glycerol, 1 mM EDTA, 3 mM mercaptoethanol) plus 50 mM KCl. The column was washed with 10 column volumes of buffer A plus 50 mM KCl and eluted with a 30 column volume gradient of buffer A from 50 mM to 1M KCl. Fractions containing polymerase activity were pooled, concentrated with a Centriprep 10 (Amicon Inc.), loaded on a 25 ml Superdex 75 FPLC column (Pharmacia), and eluted with buffer A containing 150 mM KCl.

EXAMPLE 10

Characterization of the Purified DNA Polymerase

A. Determination of the Molecular Weight of the DNA Polymerase Purified from *E. coli.*

The molecular weight of 95 kilodaltons was determined by electrophoresis in a 7.5 % polyacrylamide, SDS gel by the method of Laemmli, U.K., *Nature* (*Lond.*) 227:680–685 (1970). A single protein band was detected by silver staining (Bio-Rad).

B. Method for Measuring Incorporation of [$^{35}$S]dATPαS Relative to $^{3}$H-dATP.

In a double label experiment, [$^{35}$S]dATPαS (4 nM) was competed against $^{3}$H-dATP (1 μM) for incorporation into acid insoluable DNA by the Desulfurococcus, and Taq (LTI), DNA polymerases. The reaction contains 50 uM dCTP, dGTP, and dTTP, 10 mM Tris HCl, pH 8, 1 mM $MgCl_2$ and 1 nM DNase I activated calf thymus DNA and was incubated 5 min at 70° C. Incorporation values are normalized to the nucleotide concentration in the reaction mix generating an "insertion frequency", I(dATP)/I([$^{35}$S]dATPαS).

$$\frac{I(dATP\alpha S)}{I(dATP)} = \frac{\text{pmol dATP}\alpha S}{\text{pmol dATP}} \quad \frac{[dATP]}{[dATP\alpha S]}$$

The Desulfurococcus DNA polymerase incorporated [$^{35}$S]dATPαS relative to dATP at a frequency at least 7 times greater than for Taq DNA polymerase.

EXAMPLE 11

Sequencing with the DNA Polymerase

Conventional DNA sequencing with the DNA polymerase lacking 3'–5' exonuclease activity (purified to homogeneity by same method as Example 9) was carried out with a 5 rain reaction at 70° C. using 1 unit of DNA polymerase, and 0.1 pmol (DNA molecules) of M13 ssDNA primed with 5'-$^{32}$P-labeled 23 mer (BRL/Gibco) with 40 μM dATP, dTTP, dGTP and dCTP, and 400 μM of either ddATP, ddTTP, ddGTP or ddCTP with 10 mM Tris HCl, pH 8.0, and 1 mM $MgCl_2$. Reactions were electrophoresed as described (Adams et al., *Focus* 3:56 (BRL/Gibco).

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which this invention pertains. All cited publications and patent applications are herein incorporated by reference to the same extent as if each individual publication or patent application was specifically and individually indicated to be incorporated by reference.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 1193 base pairs
( B ) TYPE: nucleic acid
( C ) STRANDEDNESS: both
( D ) TOPOLOGY: linear ( i x ) FEATURE:
( A ) NAME/KEY: CDS
( B ) LOCATION: 6..1193

( x i ) SEQUENCE DESCRIPTION: SEQ ID NO:1:

```
GAGTT ATG ATC CTC GAT GCT GAC TAC ATC ACC GAA GAC GGA AAG CCC      47
      Met Ile Leu Asp Ala Asp Tyr Ile Thr Glu Asp Gly Lys Pro
        1               5                   10

GTC ATA AGG GTC TTC AAG AAG GAG AAG GGC GAG TTT AAG ATA GAC TAC    95
Val Ile Arg Val Phe Lys Lys Glu Lys Gly Glu Phe Lys Ile Asp Tyr
 15                 20                  25                  30

GAC AGG ACT TTC GAG CCC TAC ATC TAC GCC CTC CTG AAG GAC GAT TCC   143
Asp Arg Thr Phe Glu Pro Tyr Ile Tyr Ala Leu Leu Lys Asp Asp Ser
                35                  40                  45

GCC ATT GAG GAC ATC AAG AAG ATC ACC GCC GAG AGG CAC GGC ACC ACC   191
Ala Ile Glu Asp Ile Lys Lys Ile Thr Ala Glu Arg His Gly Thr Thr
            50                  55                  60

GTT AGA GTT ACC CGG GCG GAG AGG GTG AAG AAG AAG TTC CTC GGC AGG   239
Val Arg Val Thr Arg Ala Glu Arg Val Lys Lys Lys Phe Leu Gly Arg
        65                  70                  75

CCG GTG GAG GTC TGG AAG CTC TAC TTC ACC CAC CCC CAG GAC GTT CCC   287
Pro Val Glu Val Trp Lys Leu Tyr Phe Thr His Pro Gln Asp Val Pro
    80                  85                  90

GCG ATC AGG GAC AAG ATC AGG GAG CAT CCG GCG GTT GTT GAC ATC TAC   335
Ala Ile Arg Asp Lys Ile Arg Glu His Pro Ala Val Val Asp Ile Tyr
 95                 100                 105                 110

GAG TAC GAC ATA CCC TTC GCG AAG CGC TAC CTC ATA GAC AGG GGC TTA   383
Glu Tyr Asp Ile Pro Phe Ala Lys Arg Tyr Leu Ile Asp Arg Gly Leu
                115                 120                 125

ATC CCT ATG GAG GGG GAC GAG GAG CTC AGG ATG CTC GCC TTC GAC ATC   431
Ile Pro Met Glu Gly Asp Glu Glu Leu Arg Met Leu Ala Phe Asp Ile
            130                 135                 140

GAG ACG CTC TAC CAT GAT GGG GAG GAG TTT GGC GAG GGG CCT ATC CTG   479
Glu Thr Leu Tyr His Asp Gly Glu Glu Phe Gly Glu Gly Pro Ile Leu
        145                 150                 155

ATG ATA ACG TAC GCC GAT GAA GAG GGA GCG CGC GTT ATC ACC TGG AAG   527
Met Ile Thr Tyr Ala Asp Glu Glu Gly Ala Arg Val Ile Thr Trp Lys
    160                 165                 170
```

-continued

```
AAT ATC GAC CTC CCC TAC GTG GAG AGC GTT TCC ACC GAG AGA GAG ATG      575
Asn Ile Asp Leu Pro Tyr Val Glu Ser Val Ser Thr Glu Arg Glu Met
175                 180                 185                 190

ATA AAG CGC TCC CTC AAG GTA ATC CAG GAG AAG GAT CCC GAT GTG CTC      623
Ile Lys Arg Ser Leu Lys Val Ile Gln Glu Lys Asp Pro Asp Val Leu
            195                 200                 205

ATA ACC TAC AAC GGC GAC AAC TTC GAC TTT GCC TAC CTC AAG AAG CGC      671
Ile Thr Tyr Asn Gly Asp Asn Phe Asp Phe Ala Tyr Leu Lys Lys Arg
        210                 215                 220

TCA GAA ATG CTC GGC GTC AAG TTT ATC CTC GGA AGG GAC GGG AGC GAA      719
Ser Glu Met Leu Gly Val Lys Phe Ile Leu Gly Arg Asp Gly Ser Glu
    225                 230                 235

CCA AAA ATT CAG CGC ATG GGA GAC CGC TTT GCG GAG GTG AAG GGG AGA      767
Pro Lys Ile Gln Arg Met Gly Asp Arg Phe Ala Glu Val Lys Gly Arg
240                 245                 250

ATA CAC TTC GAC CTC TAC CCG GTT ATA AGG AGG ACG ATT AAC CTT CCC      815
Ile His Phe Asp Leu Tyr Pro Val Ile Arg Arg Thr Ile Asn Leu Pro
255                 260                 265                 270

ACC TAC ACC CTC GAG ACA GTC TAC GAG CCG GTT TTT GGG CAA CCA AAG      863
Thr Tyr Thr Leu Glu Thr Val Tyr Glu Pro Val Phe Gly Gln Pro Lys
                275                 280                 285

GAG AAG GTC TAC GCG GAA GAG ATA GCG CGG GCC TGG GAG AGC GGG GAA      911
Glu Lys Val Tyr Ala Glu Glu Ile Ala Arg Ala Trp Glu Ser Gly Glu
            290                 295                 300

GGC TTG GAA AGG GTG GCC CGC TAT TCC ATG GAG GAC GCA AAG GCA ACT      959
Gly Leu Glu Arg Val Ala Arg Tyr Ser Met Glu Asp Ala Lys Ala Thr
        305                 310                 315

TAC GAA CTC GGC AAA GAG TTC TTC CCG ATG GAG GCC CAG CTC TCG CGC     1007
Tyr Glu Leu Gly Lys Glu Phe Phe Pro Met Glu Ala Gln Leu Ser Arg
    320                 325                 330

CTC GTG GGC CAG AGC CTC TGG GAT GTA TCG CGC TCG AGC ACA GGA AAC     1055
Leu Val Gly Gln Ser Leu Trp Asp Val Ser Arg Ser Ser Thr Gly Asn
335                 340                 345                 350

TTA GTT GAG TGG TTT CTC CTG AGG AAG GCC TAC GAG AGG AAC GAC GTC     1103
Leu Val Glu Trp Phe Leu Leu Arg Lys Ala Tyr Glu Arg Asn Asp Val
                355                 360                 365

GCG CCA AAC AAG CCT GAC GAG GAG GAG TTA GCA AGG AGA GCG GAG ACG     1151
Ala Pro Asn Lys Pro Asp Glu Glu Glu Leu Ala Arg Arg Ala Glu Thr
            370                 375                 380

TAC GCG GGT GGA TAT GTC AAA GAG CCA GAA AAA GGT TTG TGG             1193
Tyr Ala Gly Gly Tyr Val Lys Glu Pro Glu Lys Gly Leu Trp
        385                 390                 395
```

( 2 ) INFORMATION FOR SEQ ID NO:2:

( i ) SEQUENCE CHARACTERISTICS:
( A ) LENGTH: 396 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asp Tyr Asp Arg
            20                  25                  30

Thr Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60
```

-continued

Val Thr Arg Ala Glu Arg Val Lys Lys Lys Phe Leu Gly Arg Pro Val
65 70 75 80

Glu Val Trp Lys Leu Tyr Phe Thr His Pro Gln Asp Val Pro Ala Ile
85 90 95

Arg Asp Lys Ile Arg Glu His Pro Ala Val Val Asp Ile Tyr Glu Tyr
100 105 110

Asp Ile Pro Phe Ala Lys Arg Tyr Leu Ile Asp Arg Gly Leu Ile Pro
115 120 125

Met Glu Gly Asp Glu Glu Leu Arg Met Leu Ala Phe Asp Ile Glu Thr
130 135 140

Leu Tyr His Asp Gly Glu Glu Phe Gly Glu Gly Pro Ile Leu Met Ile
145 150 155 160

Thr Tyr Ala Asp Glu Glu Gly Ala Arg Val Ile Thr Trp Lys Asn Ile
165 170 175

Asp Leu Pro Tyr Val Glu Ser Val Ser Thr Glu Arg Glu Met Ile Lys
180 185 190

Arg Ser Leu Lys Val Ile Gln Glu Lys Asp Pro Asp Val Leu Ile Thr
195 200 205

Tyr Asn Gly Asp Asn Phe Asp Phe Ala Tyr Leu Lys Lys Arg Ser Glu
210 215 220

Met Leu Gly Val Lys Phe Ile Leu Gly Arg Asp Gly Ser Glu Pro Lys
225 230 235 240

Ile Gln Arg Met Gly Asp Arg Phe Ala Glu Val Lys Gly Arg Ile His
245 250 255

Phe Asp Leu Tyr Pro Val Ile Arg Arg Thr Ile Asn Leu Pro Thr Tyr
260 265 270

Thr Leu Glu Thr Val Tyr Glu Pro Val Phe Gly Gln Pro Lys Glu Lys
275 280 285

Val Tyr Ala Glu Glu Ile Ala Arg Ala Trp Glu Ser Gly Glu Gly Leu
290 295 300

Glu Arg Val Ala Arg Tyr Ser Met Glu Asp Ala Lys Ala Thr Tyr Glu
305 310 315 320

Leu Gly Lys Glu Phe Phe Pro Met Glu Ala Gln Leu Ser Arg Leu Val
325 330 335

Gly Gln Ser Leu Trp Asp Val Ser Arg Ser Ser Thr Gly Asn Leu Val
340 345 350

Glu Trp Phe Leu Leu Arg Lys Ala Tyr Glu Arg Asn Asp Val Ala Pro
355 360 365

Asn Lys Pro Asp Glu Glu Glu Leu Ala Arg Arg Ala Glu Thr Tyr Ala
370 375 380

Gly Gly Tyr Val Lys Glu Pro Glu Lys Gly Leu Trp
385 390 395

( 2 ) INFORMATION FOR SEQ ID NO:3:

( i ) SEQUENCE CHARACTERISTICS:
( A ) LENGTH: 27 base pairs
( B ) TYPE: nucleic acid
( C ) STRANDEDNESS: both
( D ) TOPOLOGY: linear ( x i ) SEQUENCE DESCRIPTION: SEQ ID NO:3:

CGATCTCTAG ARAGAGARAT GATAAAG 27

( 2 ) INFORMATION FOR SEQ ID NO:4:

( i ) SEQUENCE CHARACTERISTICS:

( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:4:

CGATCGGATC CCACAAMCCY TTTTCTGGCT C 31

( 2 ) INFORMATION FOR SEQ ID NO:5:

( i ) SEQUENCE CHARACTERISTICS:
( A ) LENGTH: 36 base pairs
( B ) TYPE: nucleic acid
( C ) STRANDEDNESS: both
( D ) TOPOLOGY: linear ( x i ) SEQUENCE DESCRIPTION: SEQ ID NO:5:

CUACUACUAC UATAACATAT GATCCTCGAT GCTGAC 36

( 2 ) INFORMATION FOR SEQ ID NO:6:

( i ) SEQUENCE CHARACTERISTICS:
( A ) LENGTH: 34 base pairs
( B ) TYPE: nucleic acid
( C ) STRANDEDNESS: both
( D ) TOPOLOGY: linear ( x i ) SEQUENCE DESCRIPTION: SEQ ID NO:6:

CAUCAUCAUC AUGACTGTTG CCCAAGATCT TGAT 34

( 2 ) INFORMATION FOR SEQ ID NO:7:

( i ) SEQUENCE CHARACTERISTICS:
( A ) LENGTH: 48 base pairs
( B ) TYPE: nucleic acid
( C ) STRANDEDNESS: both
( D ) TOPOLOGY: linear ( x i ) SEQUENCE DESCRIPTION: SEQ ID NO:7:

CUACUACUAC AUTTGGCCAA CAGTTATTAC GGCTACTACG CGTACGCA 48

( 2 ) INFORMATION FOR SEQ ID NO:8:

( i ) SEQUENCE CHARACTERISTICS:
( A ) LENGTH: 36 base pairs
( B ) TYPE: nucleic acid
( C ) STRANDEDNESS: both
( D ) TOPOLOGY: linear ( x i ) SEQUENCE DESCRIPTION: SEQ ID NO:8:

CAUCAUCAUC AUATCGATAT CCGCGTAAAG CACTTT 36

( 2 ) INFORMATION FOR SEQ ID NO:9:

( i ) SEQUENCE CHARACTERISTICS:
( A ) LENGTH: 38 base pairs
( B ) TYPE: nucleic acid
( C ) STRANDEDNESS: both
( D ) TOPOLOGY: linear ( x i ) SEQUENCE DESCRIPTION: SEQ ID NO:9:

CUACUACUAC UAACTAGTAC TGACGGTTTC TTTGCCAC 38

( 2 ) INFORMATION FOR SEQ ID NO:10:

( i ) SEQUENCE CHARACTERISTICS:
( A ) LENGTH: 36 base pairs
( B ) TYPE: nucleic acid ( C ) STRANDEDNESS: both
( D ) TOPOLOGY: linear ( x i ) SEQUENCE DESCRIPTION: SEQ ID NO:10:

CAUCAUCAUC AUTGAGAATT CTTTAGCCTT ATTTTT 36

( 2 ) INFORMATION FOR SEQ ID NO:11:

( i ) SEQUENCE CHARACTERISTICS:
( A ) LENGTH: 48 base pairs
( B ) TYPE: nucleic acid
( C ) STRANDEDNESS: both
( D ) TOPOLOGY: linear ( x i ) SEQUENCE DESCRIPTION: SEQ ID NO:11:

GACGAGGAGC TCAGGATGCT CGCCTTCGCG ATCGCGACGC TCTACCAT 48

What is claimed is:

1. A substantially pure DNA polymerase comprising the amino acid sequence set forth in SEQ ID NO:2.

2. A substantially pure DNA polymerase comprising the amino acid sequence set forth in SEQ ID NO:2 except wherein asparagine at position 141 has been replaced by alanine and glutamine at position 143 has been replaced by alanine.

* * * * *